US012324877B1

(12) United States Patent
Yeheskely-Hayon et al.

(10) Patent No.: US 12,324,877 B1
(45) Date of Patent: Jun. 10, 2025

(54) BLOOD-GAS EXCHANGE DEVICE AND METHODS OF USE

(71) Applicant: Inspira-Technologies OXY B.H.N.LTD., Ra'Anana (IL)

(72) Inventors: Daniella Yeheskely-Hayon, Kibbutz Yifat (IL); Aviran Sender, Halfa (IL); Angelina Rozentsveig, Tel aviv (IL)

(73) Assignee: INSPIRA-TECHNOLOGIES OXY B.H.N. LTD, Ra'anana (IL)

( * ) Notice: Subject to any disclaimer, the term of this patent is extended or adjusted under 35 U.S.C. 154(b) by 0 days.

(21) Appl. No.: 18/747,453

(22) Filed: Jun. 19, 2024

(51) Int. Cl.
*A61M 1/32* (2006.01)

(52) U.S. Cl.
CPC ....... *A61M 1/32* (2013.01); *A61M 2202/0007* (2013.01); *A61M 2202/0014* (2013.01); *A61M 2202/0021* (2013.01); *A61M 2202/0208* (2013.01); *A61M 2202/0225* (2013.01); *A61M 2202/0266* (2013.01); *A61M 2202/0413* (2013.01); *A61M 2205/103* (2013.01)

(58) Field of Classification Search
CPC ...... A61M 1/262; A61M 1/1698; A61M 1/32; A61M 1/14; A61M 2202/0007; A61M 2202/0014; A61M 2202/0021; A61M 2202/0208; A61M 2202/0225; A61M 2202/0266; A61M 2202/0413; A61M 2202/103
See application file for complete search history.

(56) References Cited

U.S. PATENT DOCUMENTS

| | | | | |
|---|---|---|---|---|
| 3,211,148 | A * | 10/1965 | Galajda, Jr. ......... | A61M 1/3623 261/92 |
| 4,493,692 | A | 1/1985 | Reed | |
| 5,626,819 | A * | 5/1997 | Novello ................. | A61M 1/32 261/92 |
| 6,454,999 | B1 * | 9/2002 | Farhangnia ........... | F28F 21/062 604/6.14 |
| 11,793,919 | B2 | 10/2023 | Ben Noon et al. | |
| 11,938,257 | B1 | 3/2024 | Sender et al. | |

(Continued)

OTHER PUBLICATIONS

International Preliminary Report on Patentability for PCT Application PCT/IL2021/051431, prepared by the Israel Patent Office, May 30, 2023; Written Opinion of International Search Authority for PCT Application PCT/ IL2021/051431, prepared by the Israel Patent Office, Apr. 12, 2022.

(Continued)

*Primary Examiner* — Leslie R Deak
(74) *Attorney, Agent, or Firm* — The Law Office of Joseph L. Felber

(57) ABSTRACT

This invention is directed to a novel blood-gas exchange device comprising a stationary blood collecting tank, and a rotating tank, such that the stationary blood collecting tank surrounds at least part of a rotating tank. The circular movement of the rotating tank channels the inserted blood to flow along the rotatable tank wall from bottom to top, forming a blood layer on the wall that directly contacts with the gas and allows gas exchange, and wherein the stationary blood collecting tank is assembled with the rotating tank in a manner that the oxygenated and/or decarbonated blood that exit from the rotating tank through said at least one exit opening is being spilled into the stationary collecting tank and gathered to flow into a tube.

16 Claims, 11 Drawing Sheets

(56) References Cited

U.S. PATENT DOCUMENTS

| | | |
|---|---|---|
| 2007/0020142 A1* | 1/2007 | Federspiel .......... B01D 63/032 604/6.14 |
| 2010/0114005 A1 | 5/2010 | Rovatti |
| 2014/0099235 A1 | 4/2014 | Ellingboe et al. |
| 2020/0009331 A1 | 1/2020 | Kamen et al. |
| 2020/0237992 A1 | 7/2020 | Krivitski et al. |
| 2023/0338634 A1 | 10/2023 | Ben Noon et al. |

OTHER PUBLICATIONS

International Search Report for PCT Application PCT/IL2024/050751, prepared by the Israel Patent Office, Dec. 5, 2024.

Written Opinion for PCT Application PCT/IL2024/050751, prepared by the Israel Patent Office, Dec. 5, 2024.

De Somer, "Does contemporary oxygenator design influence haemolysis?", 2013, Perfusion 2013, 28(4), 280-285.

Kay et al., "The use of convoluted disks in the rotating disc oxygenator", J. Thoracic Surg., vol. 36, No. 2, pp. 268-273, Aug. 1958.

Paparella et al. "Coagulation disorders of cardiopulmonary bypass: a review", Intensive Care Med (2004), 30:1873-1881, Jul. 24, 2004.

Zangrillo et al., "A meta-analysis of complications and mortality of extracorporeal membrane oxygenation", Critical Care and Resuscitation 2013, 15(3), 172-178.

* cited by examiner

BLOOD-GAS EXCHANGE DEVICE AND METHODS OF USE

FIELD OF THE INVENTION

This invention is directed to a novel liquid-gas exchange device. More particularly, this invention is aimed to provide a revolutionary oxygenator for extracorporeal oxygenation procedures that allows the exchange of gases from the blood without a fiber-based membrane as used in common practice.

BACKGROUND OF THE INVENTION

Blood gas exchange devices are commonly used for maintaining adequate tissue oxygenation and perfusion during cardiopulmonary bypass (CPB) or extracorporeal blood circulation (ECMO) procedures. These devices function by removing blood from the body, oxygenating it and removing carbon dioxide outside the body, and then returning the oxygenated blood to the patient's circulatory system. Typical circuit contains cannulas, tubing, pump and blood gas exchange device.

The world of liquid-gas exchange devices is based today entirely on membrane technology made of hollow fibers. This technology replaced former generation of bubble oxygenators (see for example, ZA80159) that had a direct contact between the blood and the gas, however, the patient's blood was oxygenated by gas bubbles that later revealed as damaging the blood components. For the purposes of this invention the terms "Liquid-gas exchange device", "blood-gas exchange device" and "oxygenator" are all directed to the same and describe a device for exchanging at least one gas between a liquid medium and a gas phase, for example exchange of oxygen and/or carbon dioxide in the blood and may be used hereinbelow interchangeably.

For simplicity of explanation, the term "Blood" as used herein includes whole blood, blood components, plasma, and serum.

The hollow fibers oxygenators have significant limitations due to the material from which the oxygenator is made, the structure of the oxygenator and the blood flow regime. Unlike the natural laminar blood flow in blood vessels inside the body, in existing oxygenators the blood is "forced" to flow in a harmful turbulent flow through many layers of fibers, in which the gas flows within while experiencing friction and shear forces with the fiber walls. Since the fiber fabric is a major resistor to blood flow, high pressure differences are formed between oxygenator blood inlet and blood outlet (pressure drop). The existing flow regime, i.e., the unnatural turbulent flow, the high shear forces and the high pressure differences, causes significant damage to the various blood components, including, high hemolysis (breakdown of red cells), damage to white blood cells, activation of the inflammatory system in the body, activation of the immune system, and especially significant damage to the blood clotting system (for more details see: Zangrillo et al., A meta-analysis of complications and mortality of extracorporeal membrane oxygenation, *Critical Care and Resuscitation*, Volume 15, Number 3, September 2013; F. De Somer, Does contemporary oxygenator design influence haemolysis?, *Perfusion* 28 (4) 280-285, 2013; Paparella et al., Coagulation disorders of cardiopulmonary bypass: a review, *Intensive Care Med* 30:1873-1881, 2004.)

The substantial damage to blood components and the hemostasis (i.e., imbalance of the coagulation system), requires the administration of systemic anticoagulants to the patient and constant monitoring in order to prevent the accumulation of blood clots (both in the system and in the patient), neurological hemorrhages, damage to vital organs, an acute inflammatory reaction that damages vital organs and more. In recent years, many efforts have been made to develop membranes made of various materials that will enable efficient gas exchange and cause less damage, but until this moment there is no commercial oxygenator that allows the exchange of gases without a fiber-based membrane, in a way that will reduce membrane-related damages.

Blood-gas exchange device having direct contact between blood and gas has been described in the art and known as a disk oxygenator (THE USE OF CONVOLUTED DISCS IN THE ROTATING DISC OXYGENATOR by Earle B. Kay, MD., John E. Galajda, B. S., Andrew Lux, M. s., and F. S. Cross, MD., Cleveland, Ohio. J. Thoracic Surg. August 1958). However, this solution was found to cause significant damage to the oxygenated blood and consequently, not effective.

One another blood-gas exchange device that enables efficient gas exchange, without the need for a separating membrane and with direct contact between blood and gas was previously disclosed in the art by the same inventors in U.S. Pat. No. 11,938,257 incorporated herein by reference.

The oxygenator of the present invention takes the concept of direct gas exchange without the necessity of using separating membrane, a further step forward, as it is aimed to provide a powerful multidirectional oxygenator that allows insertion and exit of the blood from various directions, and it is relatively simple and highly effective for reducing trauma to the blood, thus allows to reduce the clinical complications associated with usage of traditional oxygenators.

Additionally, since the novel oxygenator provided herein does not use hollow fibers, it eliminates the dependency on a single supplier in the world and significantly reduces the production costs of the device.

In Summary, the novel oxygenator of the invention provides a revolutionary engineering design and management of the flow regime in a completely different way from the existing and accepted regime in the field of oxygenators having separating membrane, and further lower the risk levels associated with the use of oxygenators and reduces the manufacturing cost.

SUMMARY OF THE INVENTION

In one main aspect, the present invention is directed to a revolutionary technology that is aimed to divert the world of blood oxygenation from the use of technology that relies on a fiber membrane or gas bubbles and causes substantial damage to the patient's blood, towards the use of technology that allows the exchange of gases without a membrane at all and is aimed to reduces risks and improves patient outcome. The unique properties of the novel blood-gas exchange device as will be described hereinbelow enables efficient gas exchange with zero pressure differences between blood outlet and blood inlet which potentially will results in less shear stress and less damage to blood components during the gas exchange process, damage that leads to critical clinical complications such as, but not limited to hemolysis, inflammation, blood clots and more.

Thus, the present invention in one main aspect is directed to a blood-gas exchange device that comprises a) a stationary blood collecting tank, said stationary blood collecting tank surrounds at least part of a rotating tank, and comprises at least a gas inlet configured to allow flow of gas into the blood-gas exchange device, a gas exit configured to allow exit of gas out from the blood-gas exchange device; and a blood exit configured to allow flow of oxygenated and/or decarbonated blood out from the blood-gas exchange device into a tube; b) a rotating tank, said rotating tank comprises at least: a gas inlet and a blood inlet for insertion of blood and gas flow into the blood-gas exchange device for oxygenating the inserted blood and/or for removing carbon dioxide from the inserted blood; and at least one blood exit opening for removing the oxygenated and/or decarbonated blood out from the rotating tank into the stationary collecting tank; and c) a motor configured to spin said rotating tank; wherein, the circular movement of the rotating tank channels the inserted blood. to flow along the rotatable tank wall from bottom to top, forming a blood layer on the wall that directly contacts with the gas and allows gas exchange; and wherein the stationary blood collecting tank is assembled with the rotating tank in a manner that the oxygenated and/or decarbonated blood that exit from the rotating tank through said at least one exit opening is being spilled into the stationary collecting tank and gathered to flow into a tube.

In accordance with embodiments of the invention, the stationary blood collecting tank and the rotating tank are separated by at least one bearing that allows the stationary blood collecting tank to remain static. Optionally but not necessarily, the bearing allows transfer of gas from the rotating tank into the stationary blood collecting tank so as to allow release of the gas to the surroundings. In some other optional embodiments, the rotating tank comprises a dedicated opening that allows passage of the gas into the stationary collecting chamber and release to the surroundings.

Yet, in accordance with one another embodiment, the blood-gas exchange device is further comprising a blood inlet chamber that is functionally connected to the rotating chamber and configured to allow insertion of blood into the rotating tank from the bottom.

Optionally, the rotating tank topping comprises at least one gas opening configured to allow the gas inserted through the blood collecting tank to flow into the rotating tank so as to allow gas exchange with the flowing blood, and further to allow exit of gas following the gas exchange with the blood back into said blood collecting tank for release of the gas to the surroundings.

Yet, in one another optional embodiment of the invention, the stationary collecting tank is fully surrounding the rotating tank, and further comprising a blood inlet for insertion of blood into the rotating tank for oxygenating the blood and/or for removing carbon dioxide from the blood. In such embodiment, the blood is inserted into the blood-gas exchange device from the blood inlet of said stationary blood collecting tank, flowed into the rotating tank for gas exchange, and returns to the blood collecting tank upon oxygenation and/or removal of carbon dioxide and gathered to flow into a tube or directly into another chamber for storage or else.

The blood layer created on the inner wall of the rotating tank may be a blood channel or a blood film formed by the circular movement of the rotatable tank. Preferably, the blood layer flows upward against gravity force by the circular movement of the rotatable tank.

The gas inlet is configured to insert into the blood-gas exchange device either one of the following gases: pure oxygen, air, enriched air with oxygen at various ratios, nitrogen, carbon dioxide and mixture thereof. All according to a specific need and/or operating protocol.

In further embodiments of the invention, the blood-gas exchange device further comprises at least one perforated gas column configured to inflow the gas inserted through the gas inlet of the stationary blood collecting tank into the rotating tank, said at least one perforated gas column is positioned within the rotating tank cavity and allows flow of gas from the column toward the flowing blood. The exchanged gas may flow out through openings in the ceiling, through the bearing or it can flow into the perforated gas column.

The gas exchange as mentioned above may be either oxygenation of the blood or decarbonation of the blood or a combination thereof.

Yet, in accordance with embodiments of the invention, the blood inlet and blood exit, each is preferably connected to a tube that delivers blood from a blood source and/or from a storage container into the blood-gas exchange device and returns the blood to the blood source and/or to a storage container following the gas exchange via the blood exit.

Optionally, the blood-gas exchange device further comprises at least one pump configured to withdraw blood from said blood source or from the storage container into the blood-gas exchange device and to transfer the oxygenated/decarbonated blood back to the blood exit.

Preferably, the flow of gas through the gas inlet and the exit of gas through the gas exit is continuous and allows a gradient flow of gases within the blood-gas exchange device that enables gases from the blood to diffuse into the rotatable tank and gases from the rotatable tank to diffuse into the flowing blood.

In some optional embodiments of the invention another body fluid may be inserted for gas exchange procedure into the blood-gas exchange device instead of blood. In addition, the blood-gas exchange device of the invention may be used for various systems and procedures including without limitation extracorporeal life support systems (the device may be used during procedures such as ECMO and cardiopulmonary bypass), intravascular oxygenation systems, and implanted oxygenating and/or gas exchanging devices.

The blood-gas exchange device of the invention may be used mutatis mutandis with other liquids, for example instead of blood another body fluid such as plasma may be inserted for gas exchange procedure.

BRIEF DESCRIPTION OF THE DRAWINGS

Examples illustrative of embodiments of the disclosure are described below with reference to figures attached hereto. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings.

The figures (FIGS.) are listed below.

FIG. 2A illustrates a conical rotating tank while FIG. 2B illustrates cylindrical rotating tank.

FIGS. 4A-4C are schematic illustrations of one another optional embodiment of the novel oxygenator of the invention having an upper motor connected to the rotating tank with a belt, wherein FIG. 4A is an isometric view; FIG. 4B is a cross section view; and FIG. 4C is an isometric cross section exploding view.

FIGS. 5A-5B are schematic illustrations showing the oxygenator assembly of the invention positioned leaning on a stand in a manner that the blood entered into the oxygenator hits the tank's wall and not the tank's floor as illustrated before, wherein, FIG. 5A is an isometric side view illustration of the assembly tilted on a stand; FIG. 5B is a cross section view illustrating of the assembly of FIG. 5A showing the tank rotation direction and the blood flow from entrance to exit.

DETAILED DESCRIPTION OF EMBODIMENTS OF THE INVENTION

In the following description, various aspects of the novel blood-gas exchange device of the invention will be described. For the purpose of explanation, specific configurations and details are set forth in order to provide a thorough understanding of the invention.

Although various features of the disclosure may be described in the context of a single embodiment, the features may also be provided separately or in any suitable combination. Conversely, although the disclosure may be described herein in the context of separate embodiments for clarity, the disclosure may also be implemented in a single embodiment. Furthermore, it should be understood that the disclosure can be carried out or practiced in various ways, and that the disclosure can be implemented in embodiments other than the exemplary ones described herein below. The descriptions, examples and materials presented in the description, as well as in the claims, should not be construed as limiting, but rather as illustrative. The oxygenator provided herein may be used as part of an extracorporeal oxygenation system and may be used in operating rooms and intensive care units in hospitals.

The oxygenator allows efficient and safe gas exchange without the membrane present in commercial oxygenators available in the market.

In accordance with one embodiment of the invention the oxygenator is a disposable device, designed to be used in a single patient. The components that are in direct contact with the patient's blood are manufactured from biocompatible materials, i.e., from materials approved for direct contact with blood, such as but not limited to stainless steel and polycarbonate. All components are preferably coated with anti-coagulation materials to enable long-term operation.

The oxygenator may be designed to fit with high flow extracorporeal oxygenation systems or low flow extracorporeal oxygenation systems as described by the applicant in PCT/IL2021/051431. Additionally, the oxygenator provided herein can fit both short term operations (such as Cardio-pulmonary Bypass (CPB)), and long duration operation (such as Extracorporeal Membrane Oxygenation (ECMO)).

Examples illustrative of embodiments of the disclosure are described below with reference to figures attached hereto. Dimensions of components and features shown in the figures are generally chosen for convenience and clarity of presentation and are not necessarily shown to scale. Many of the figures presented are in the form of schematic illustrations and, as such, certain elements may be drawn greatly simplified or not-to-scale, for illustrative clarity. The figures are not intended to be production drawings.

Figure 1A:
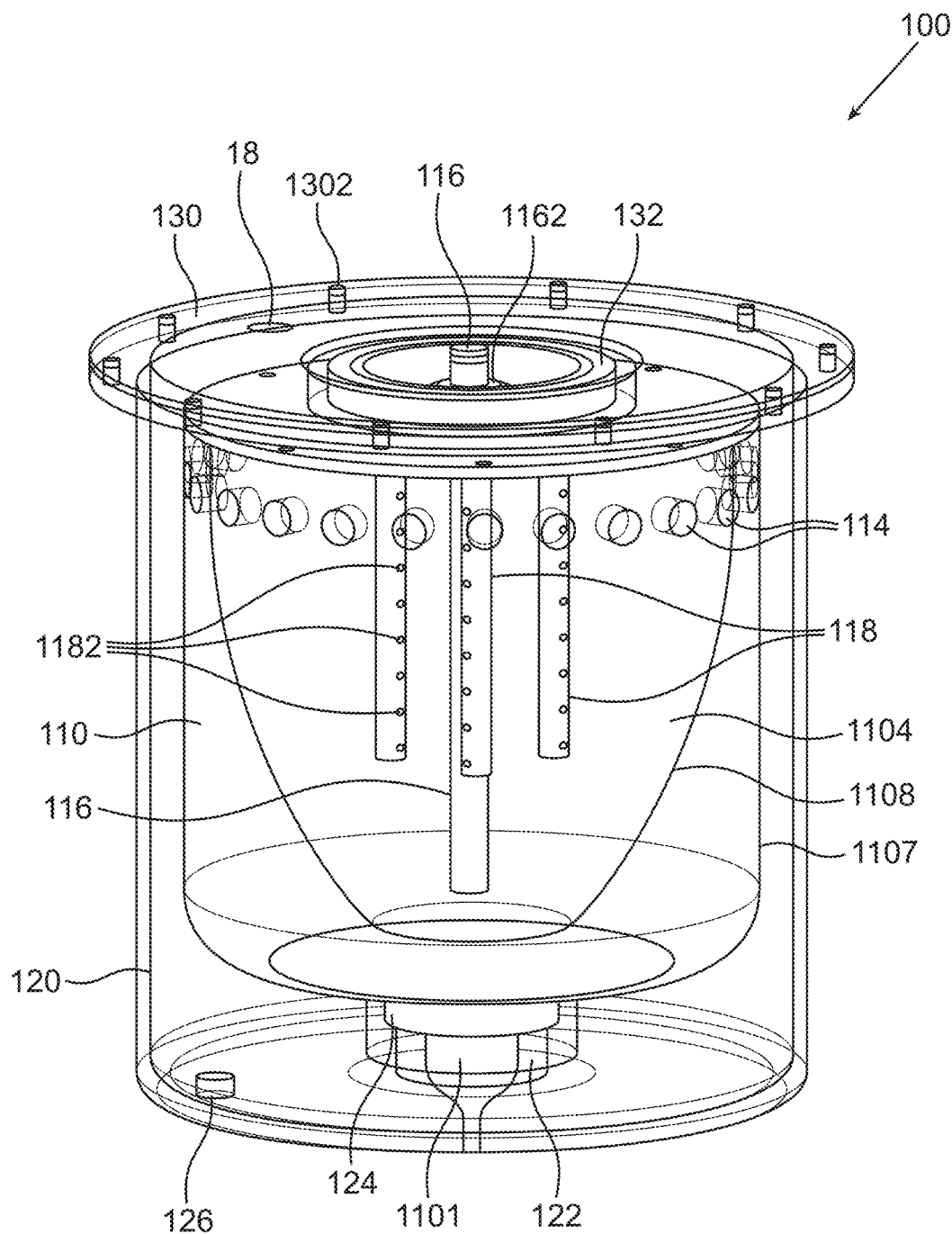
FIG. 1A is a schematic isometric view of a novel oxygenator according to one optional embodiment of the invention.
Figure 1B:
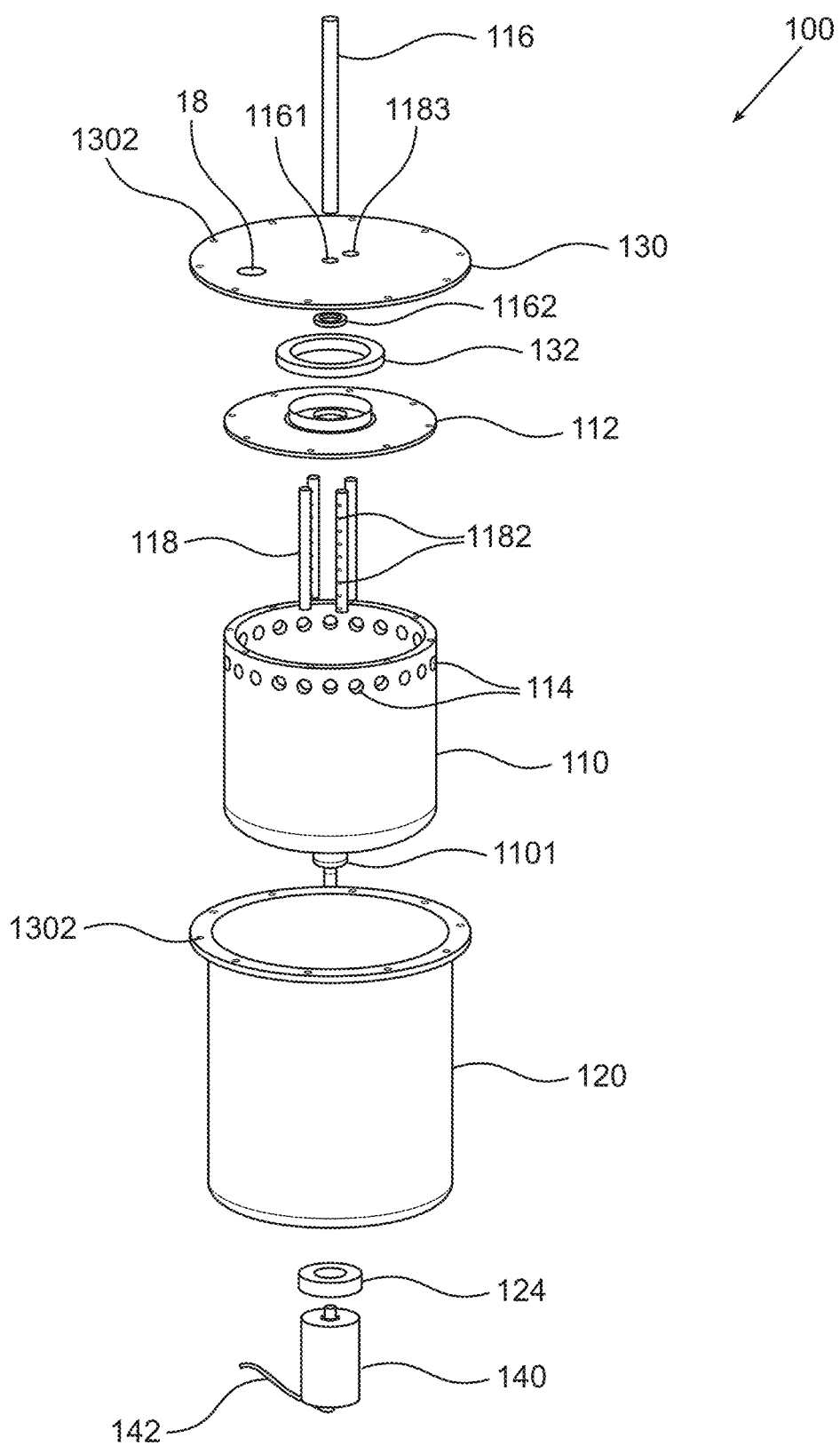
FIG. 1B is a schematic exploding view illustration of the novel oxygenator of FIG. 1A.

Reference is now made to the drawings:

FIGS. 1A and 1B are schematic isometric view and exploding view illustrations of a novel oxygenator 100 respectively, according to one optional embodiment of the invention. The oxygenator 100 comprises at least a rotating tank 110 and a blood collecting tank 120. In the specific non-limiting embodiment illustrated in this drawing rotating tank 110 is positioned within blood collecting tank 120.

Rotating tank 110 can be designed in various configurations. In the specific embodiment illustrated herein, inner wall 1108 of rotating tank 110 has a conical shape, while the outer wall 1107 of rotating tank 110 has a cylindrical shape that is compatible with the cylindrical shape of blood collecting tank 120 that "envelopes" rotating tank 110. Rotating tank 110 comprises at its upper section at least one blood drainage opening 114. In the specific example illustrated herein, rotating tank 110 comprises plurality of blood drainage openings 114 shaped as round holes. The bottom section 1101 of rotating chamber 110 is narrowed and configured to be connected to motor 140 that may be connected to electric source by electric cable 142. Alternatively, motor 140 may be wirelessly charged or operated by a dedicated battery. Alternatively, the motor is operated by magnetic coupling.

Bottom section 1101 is passing through a dedicated opening 122 at the bottom of blood collecting tank 120. Blood collecting tank 120 further comprises blood exit opening 126 that is configured to be connected to a tube that returns the oxygenated blood back to the patient's body. Also shown in this drawing collecting blood tank bearing 124 that is aimed to separate the rotation movement of rotating tank 110 from blood collecting tank 120 that covers it and to ensure the stationarity of blood collecting tank 120.

Blood collecting tank 120 is covered at the top portion by a top cover 130. Top cover 130 may be connected to blood collecting tank 120 by various attachment means, such as but not limited to screws, weldment, glue, and any other attachment means that is suitable with this invention. A non-limiting example shown in these drawings is attachment by screws. In such embodiment, holes 1302 for screws are made in top cover 130 and at the upper edge of blood collecting tank 120. Top cover 130 comprised at least an opening 1183 for gas entry and an opening 18 for gas release back into the environment following the gas exchange process or for the release of excessive gas. In the specific embodiment illustrated herein, top cover 130 further comprises additional opening 1161 for blood entrance (all openings are shown in FIG. 1B). Blood from the patient is delivered into oxygenator 100 for oxygenation and for removal of carbon dioxide through blood inlet tube 116 that passes through blood inlet tube opening 1161. In some other optional embodiments of the invention the blood may enter into the oxygenator through a dedicated blood inlet chamber or into the rotating tank. The blood reaches the bottom section of rotating tank cavity 1104 and thanks to the rotation movement it flows upward in a centrifugal manner thereby spreading over the rotating tank inner wall 1108 in thin layer that enables an effective gas exchange as will be described in detail herein below. The oxygenated blood reaches the upper portion of rotating tank 110 and exit the rotating chamber through drainage holes 114 into collecting chamber 120, and further removed from the collecting chamber back to the patient by a tube (not shown) that connects to blood exit opening 126. During that flow of the blood within the rotating chamber from entrance until it exits into the blood collecting tank the gas from the gas columns flows toward the deoxygenated blood and gas exchange is performed, such that oxygen enters the blood and carbon dioxide is released from the blood. As the time flow duration along the inner wall from bottom to top extends, the oxygenation time of the blood extends substantially as well.

Gas, preferably pure oxygen, or air, or enriched air with oxygen (or any other desired gas according to the use) flows, preferably by pressure, into oxygenator 100 through opening 1183 and continues into the space created between top cover 130 and rotating middle plate 112 that function as the ceiling of rotating tank 110. The accumulated gas flows through at least one gas tube 118 that is attached to the bottom side of rotating middle plate 112 extending into rotating tank cavity 1104. Gas tube 118 comprises plurality of apertures 1182 to release the gas from gas tube 118 into rotating tank cavity 1104 to thereby allow gas exchange with the blood that flows on inner wall 1108 of rotating tank 110. In the specific embodiment illustrated in FIG. 1A-1B oxygenator 100 comprises four gas tubes 118. However, the number of gas tubes may vary according to the specific design of the oxygenator and the designer decision, and even can be reduced in some optional embodiments to zero as illustrated in FIGS. 4A-4D. In some optional embodiments the novel oxygenator may comprise sensors. In some other optional embodiments of the invention, a gas mixer may be used. The gas mixer may flow gases in a precise and controlled manner as required and may interface with the oxygenator's controller and/or with an extracorporeal oxygenation system controller as well as with other various sensors.

Besides collecting the blood, chamber 120 also allows release of the gases accumulated in the rotatable chamber inner space 1104 out to the surrounding through gas exit opening 18 that allows the release of the exchanged gas or the excessive gas back to the surroundings. Alternatively, or additionally, gas may be released to the surroundings through the bearings instead of a dedicated gas release opening 18, or through both.

To keep blood inlet tube 116 stationary, blood inlet bearing 1162 separates between rotating middle plate 112 and blood inlet tube 116 such that the rotation movement is being clogged by bearing 1162. Similar function is obtained by top cover bearing 132 separates between rotating middle plate 112 that is part of rotating tank 110, and top cover 130 that is part of the stationary collecting tank 120.

Blood from the patient and gas from gas resource enters through dedicated tubes into rotating tank cavity 1104. Due to the rotation movement the entered blood is directed to flow onto the inner wall 1108 of rotating tank 110, from the bottom of the tank upward. The blood is being spread on the inner wall 1108 in a thin layer that allows gas exchange between the blood and the gas that was entered into the same cavity and being spread within, such that Carbon dioxide ($CO_2$) is removed from the blood and Oxygen ($O_2$) is being transferred to the blood. The gas exchange occurs along the movement of the blood on inner wall 1108 in a manner that the upper the blood flows the Oxygen level increase and the Carbon dioxide level decrease, and when the blood reaches the blood drainage openings 114 at the upper portion of rotating tank 110, the gas composition within the blood is suitable to be returned to the patient's body. The oxygenated blood accumulates in blood collecting tank 120 and exit through a tube connected to blood exit opening 126 to be circulated back into the patient.

Figure 1C:
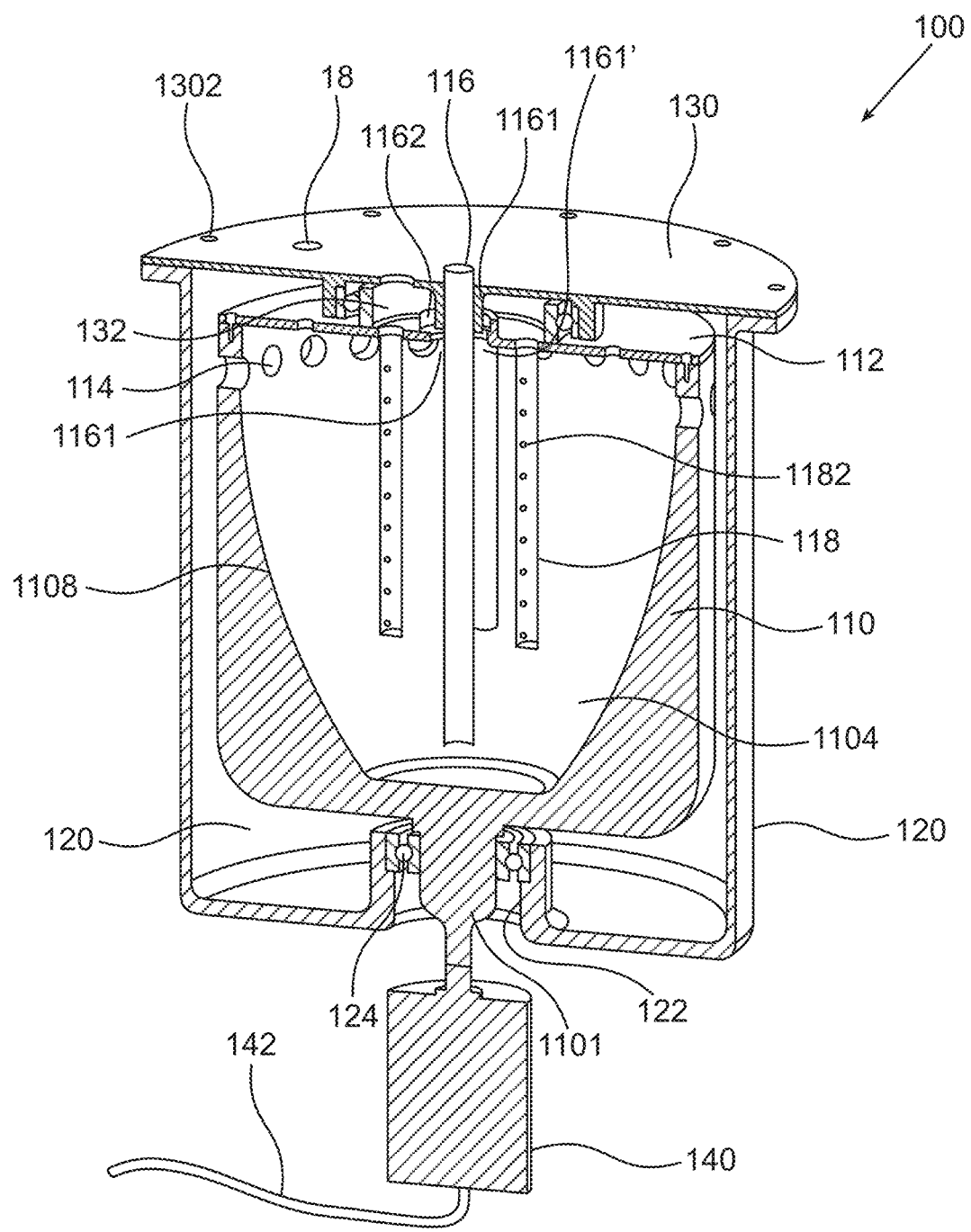
FIG. 1C is a schematic cross section view illustration of the novel oxygenator of FIG. 1A.

FIG. 1C is a schematic cross section view illustration of the novel oxygenator 100 of FIGS. 1A-1B. shown in this view are rotating tank 110 sealed by rotating middle plate 112 and encompassed by blood collecting tank 120.blood collecting tank 120 is sealed with top cover 130 by screws attached through holes 1302 along the perimeter of top cover 130. Rotating tank 110 is separated from stationary blood collecting tank 120 by top cover bearing 132 on top, and by collecting tank bearing 124 at the bottom. Also shown in this drawing are gas release opening 18 and blood inlet tube 116 that crosses through top cover 130 and rotating middle plate 112 through openings 1161 and 1161' respectively and remains stationary thanks to blood inlet bearing 1162. Blood inlet tube 116 extends downward into rotating tank inner cavity 1104 and directed to flow on the inner wall 1108 of rotating tank 110 due to the circulation of tank 110. Also shown in this view are gas tubes 118 with gas release apertures 1182, and blood drainage openings 114. The bottom area of rotating tank 1101 is narrow and passes through bottom opening 122 of blood collecting tank 120 to thereby connect to motor 140 connected to power source through electric cable 142.

Figures 2A, 2B:
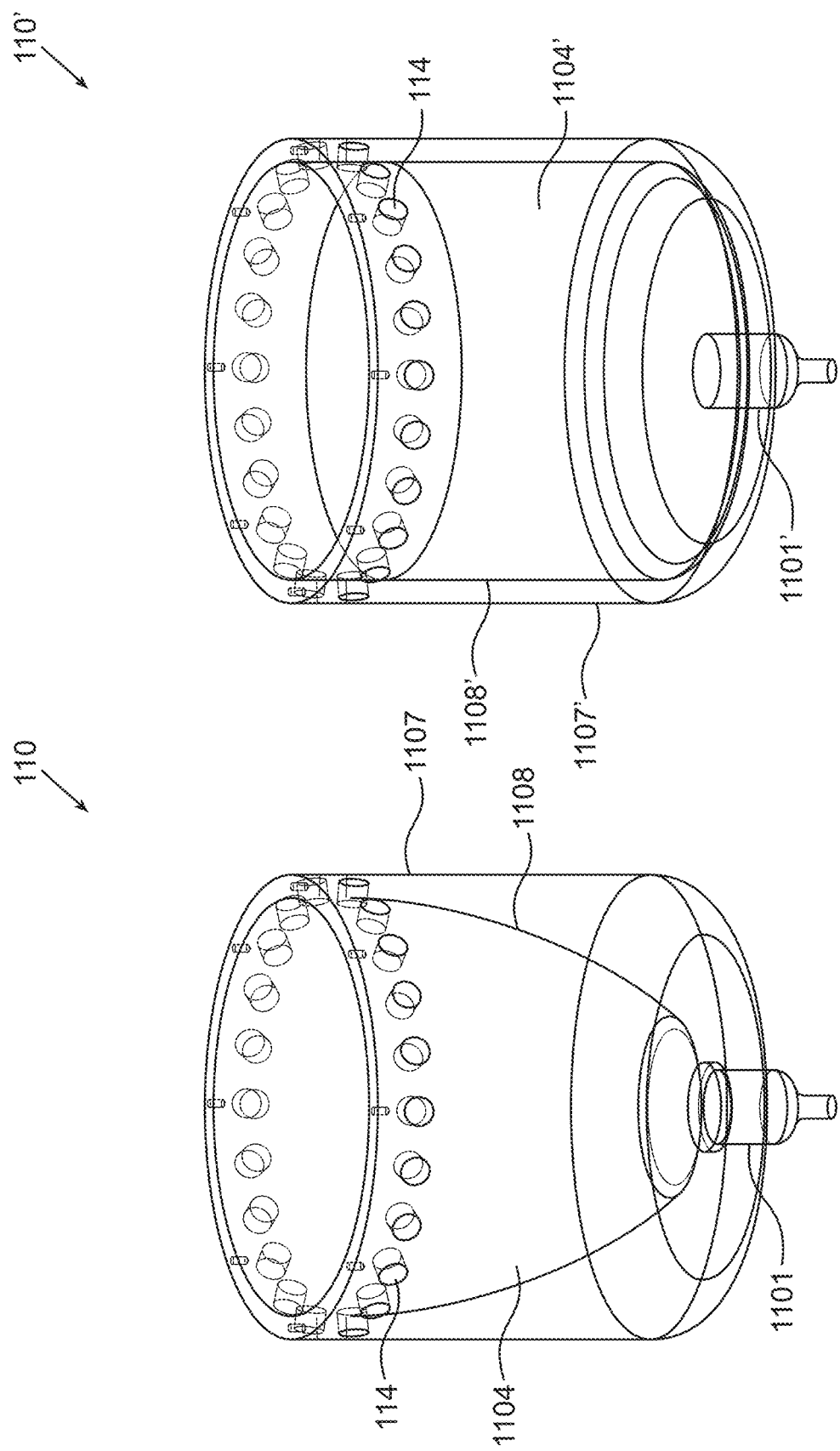
FIGS. 2A-2B are schematic illustrations of two optional structural embodiments of the rotating tank.

FIGS. 2A-2B are schematic illustrations of two optional structural embodiments of rotating tank 110 and 110' respectively. FIG. 2A illustrates rotating tank 110 of FIG. 1A characterized by having inner wall 1108 having a conic shape and outer wall 1107 having a cylindrical shape. The inner cavity 1104 of rotating tank 110 is conical thanks to the inner wall shape. One another optional embodiment is illustrated in FIG. 2B of cylindrical rotating tank 110' that having similar shaped inner and outer wall 1108' and 1107' respectively. In this embodiment, inner cavity 1104' has a cylindrical shape as well. Also shown in these drawings are bottom sections 1101 and 1101' of rotating tanks 110 and 110' respectively, and blood drainage openings 114 positioned at the upper portion of rotating tanks 110 and 110' so as to ensure that the blood that exit through these holes and collected by the collecting tank is oxygenated blood with gas content that is suitable to be circulated back into the patient's body.

Figure 2C:
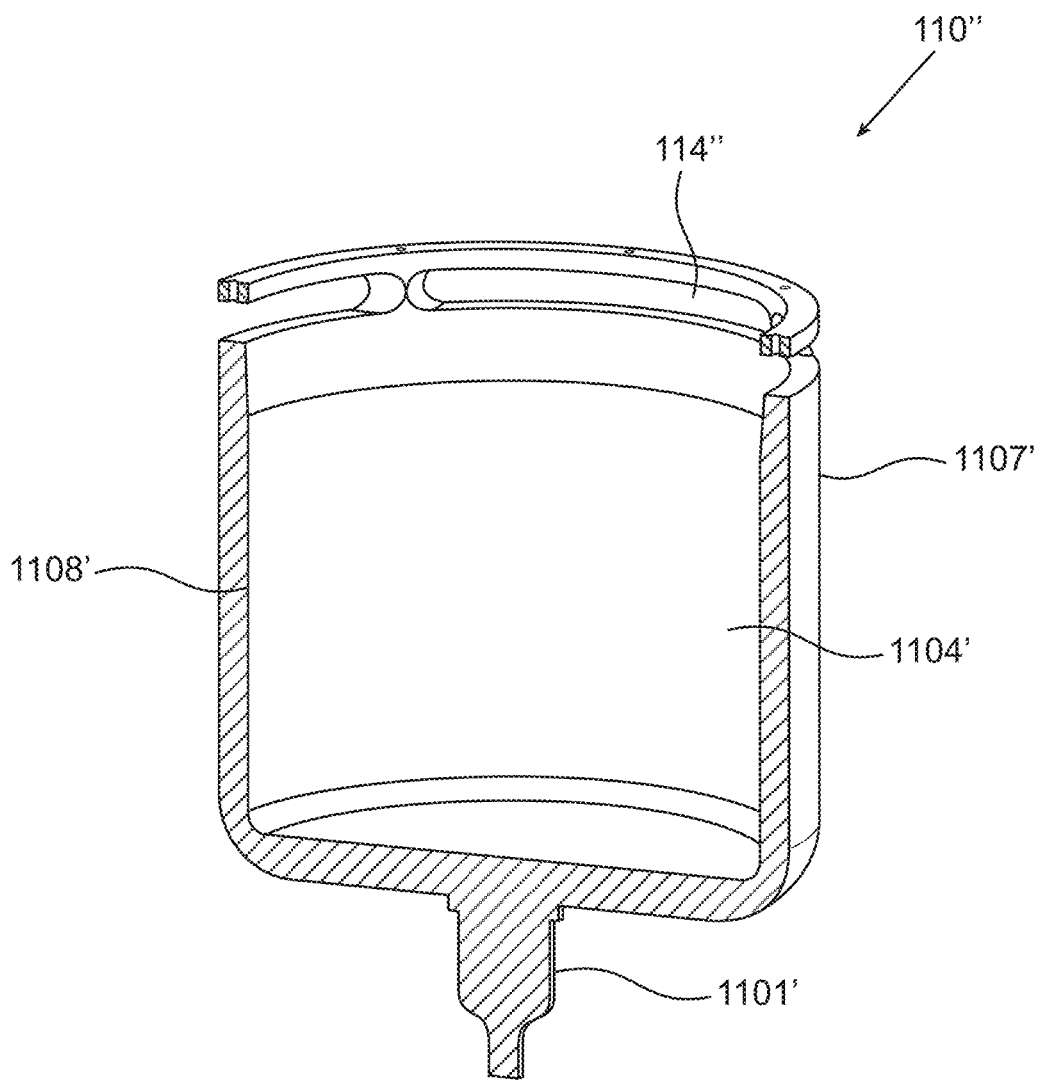
FIG. 2C illustrates additional embodiment of a rotating tank having elongated blood opening slots.

FIG. 2C illustrates an additional embodiment of cylindrical rotating tank 110' of FIG. 2B having elongated blood drainage slots 114'' instead of the circular holes 114. In all variations, the blood drainage openings are positioned at the upper portion of the rotating tank to ensure that the blood that exits through these openings and collected by the collecting chamber has completed the gas exchange process and is ready to be circulated back into the patient. Also shown in this cross section are outer wall 1107', inner wall 1108', inner cavity 1104' and bottom section 1101' of rotating tank 110'.

Figure 3A:
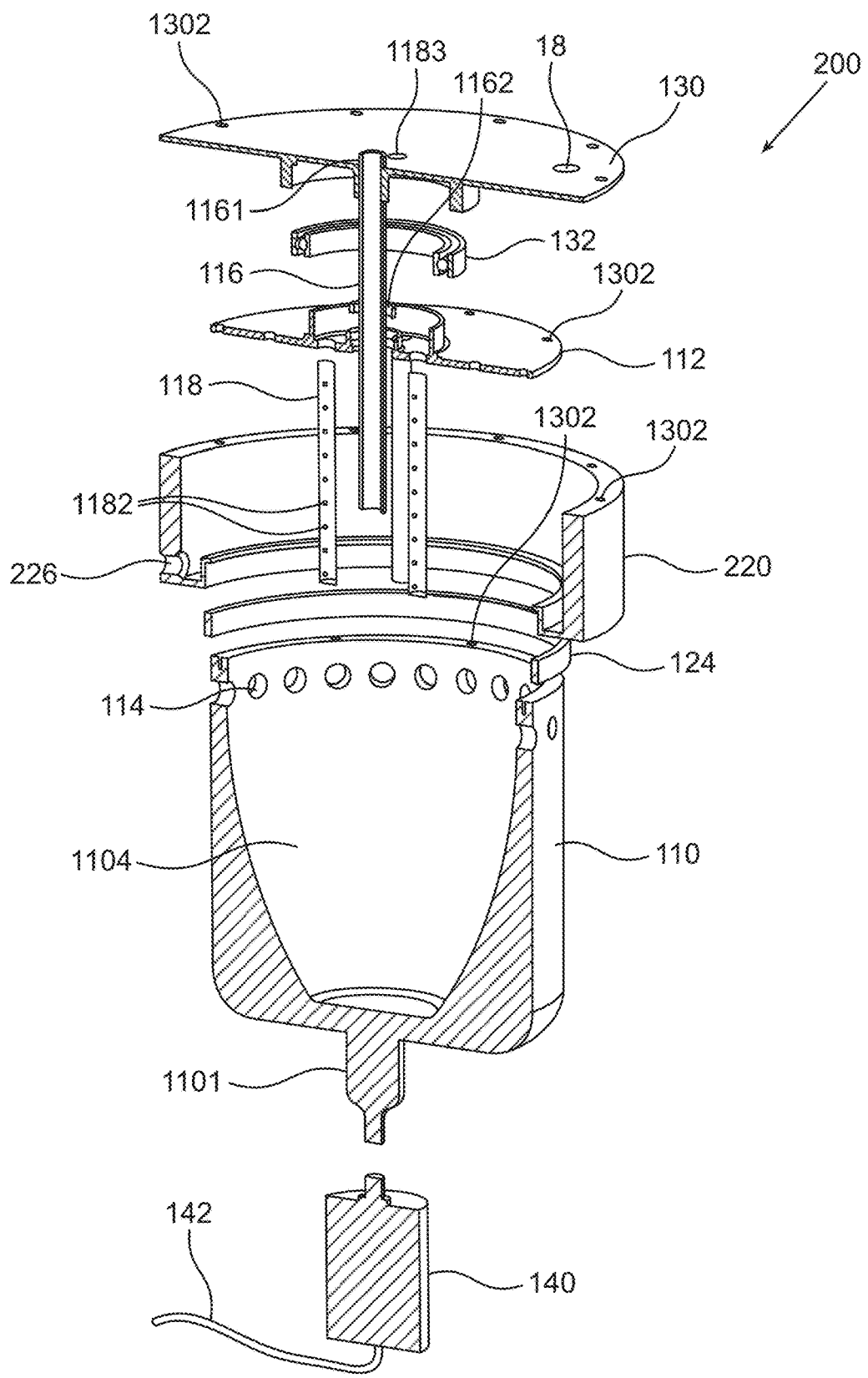
FIGS. 3A-3B are schematic exploding view and cross section view illustrations of one another optional embodiment of the novel oxygenator of the invention having an upper collecting tank.
Figure 3B:
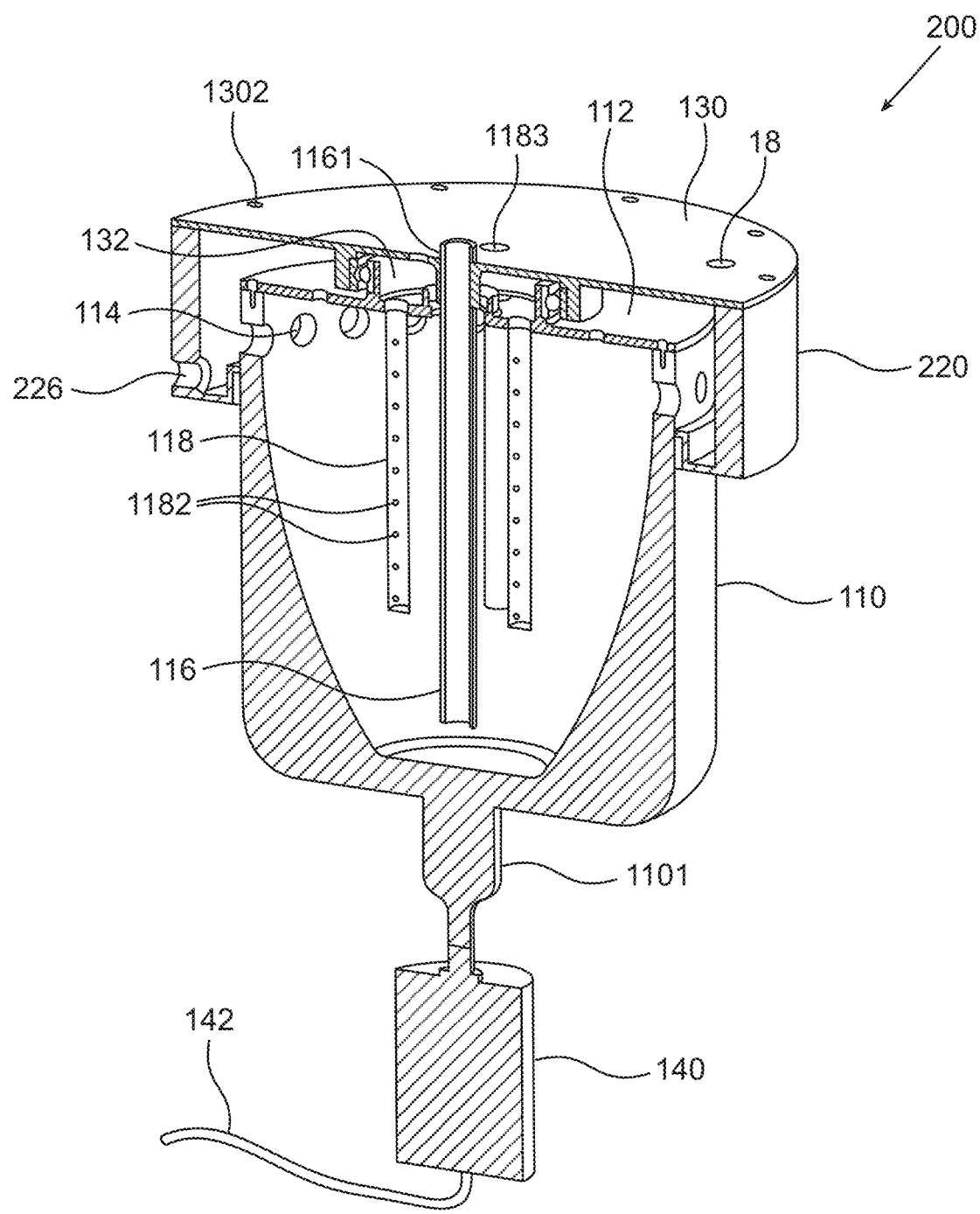

FIGS. 3A-3B are schematic exploding view illustration and cross section view illustration respectively, of oxygenator 200 in accordance with some optional embodiments of the invention having an upper collecting tank 220.

In more detail, in the embodiment illustrated in these drawings, rotating tank 110 is similar to the rotating tank illustrated in FIGS. 1A-1C, while blood collecting tank 220 is positioned on top of rotating tank 110 in a manner that covers only the upper portion of rotating tank 110 including blood drainage openings 114. In the non-limiting embodiment illustrated herein, upper blood collecting tank 220 is shaped as a perimetric container that covers the upper portion of rotating tank 110, sealed by top cover 130 that comprises opening 1183 for gas entrance into oxygenator 200, gas release opening 18, and opening 1161 for entering blood inlet tube 116 that circulates blood from the patient into the oxygenating device. Similar to the embodiment described above in detail with reference to FIGS. 1A-1C oxygenator 200 is based on the concept that the blood collecting tank 220 is stationary and embraces at least part of the rotating tank 110, while the rotating tank allows efficient gas exchange of the inserted blood thanks to the rotation movement of the tank that mimic centrifugal forces, and enforce the blood entered through blood inlet tube 116 to flow from the bottom of the rotating tank upward along the inner wall, and during that flow of the blood along the wall, the gas exchange process occurs as described in detail above. When the blood reached drainage openings 114, the gases concentration in the blood are suitable to re-circulate the blood back to the patient. In other words, the blood that enters rotating tank 110 has low Oxygen levels and high Carbon dioxide levels, while the blood that exits from rotating tank 110 has high Oxygen levels and low Carbon dioxide levels. The oxygenated blood is accumulated in blood collecting tank 220 and exit through opening 226 that is configured to be connected to a tube for circulating it back to the patient. Also shown in these drawings are top cover bearing 132 and blood inlet bearing 1162 that are aimed to keep blood collecting chamber 220 and blood inlet tube 116 stationary while rotating tank 110 circulates. Bearing 132 separates between top cover 130 and rotating middle plate 112 that serves as the ceiling of rotating tank 110. Holes 1302 for attachment of the covers to their chambers by screws are also shown. Bearing 124 in this configuration is positioned higher relative to the motor at the contact line of rotating tank 110 band blood collecting tank 220, and its dimensions are broader and fitting to the dimensions of collecting tank 220. Bottom section 1101 of rotating tank 110 is connected to motor 140 and electric cable 142 Gas tubes 118 with gas release holes 1182, and cavity 1104 are also shown.

It should be clear that the above embodiment is only one another optional configuration for implementation of the present invention and should not be construed as limiting other optional configurations. For example, rotating tank 110 could be cylindrical as illustrated in FIG. 2B or in any other geometrical shape, as long as it fits with the concept of the present invention. Additionally, the blood collecting tank may have different shape and may be positioned in other orientations relative to the rotating tank, may be designed in various shapes as long as they're compatible with the concept of the present invention as explained above, and the examples provided herein should not be construed as limiting the scope of this invention in any manner. For example, it may be positioned on the side the of rotating tank and as long as the functionality of the tanks as described in detail above maintains it should be considered as part of this invention.

Figure 4A:
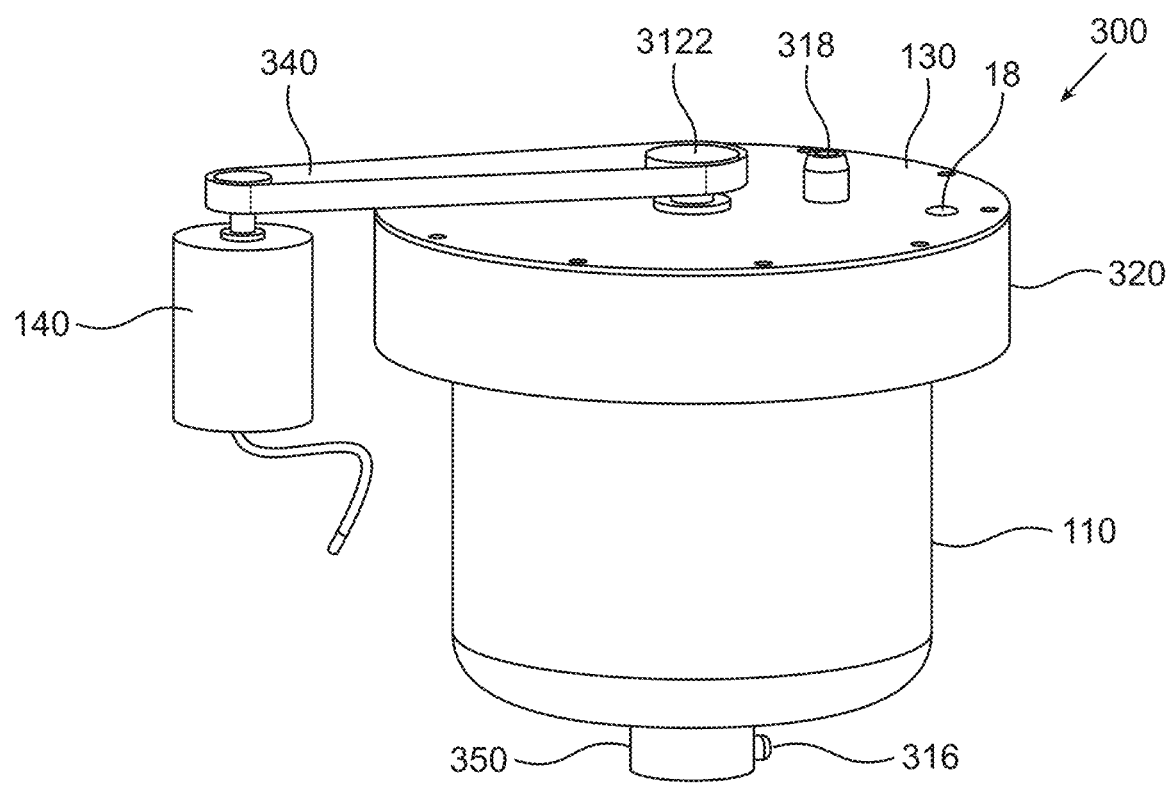
Figure 4B:
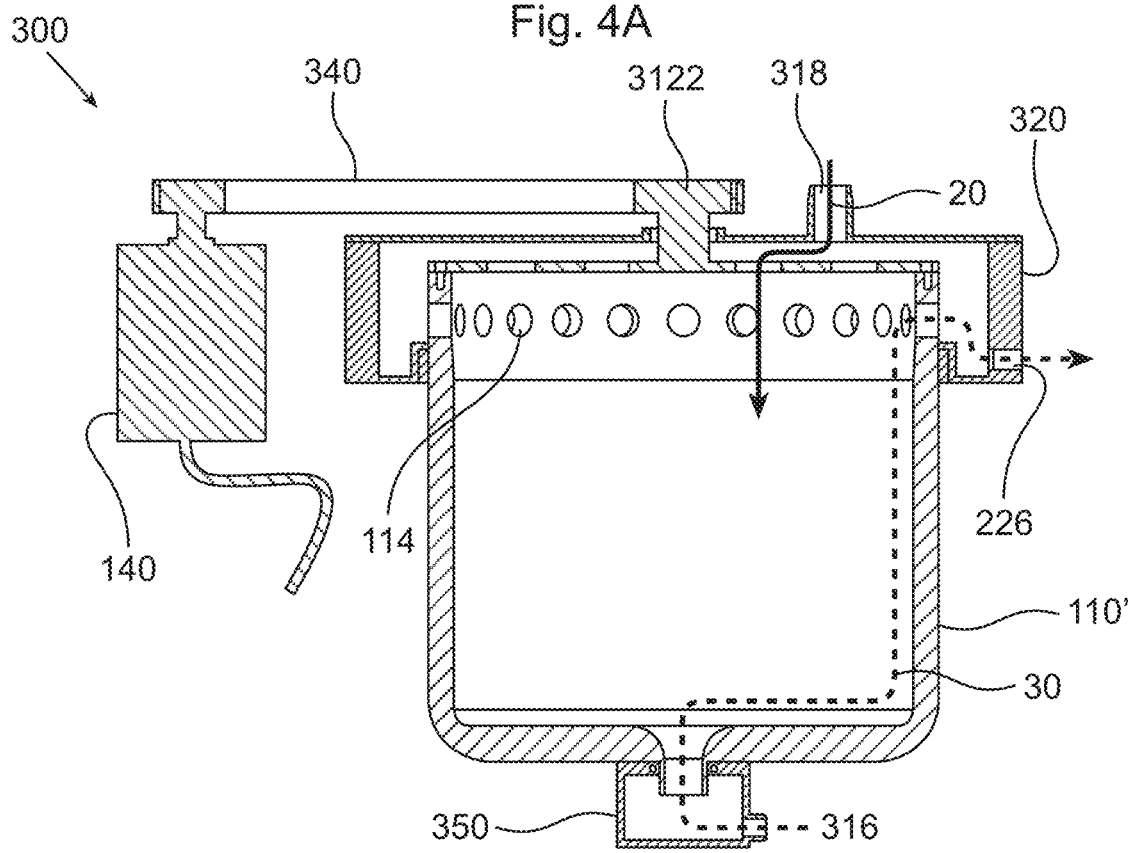
Figure 4C:
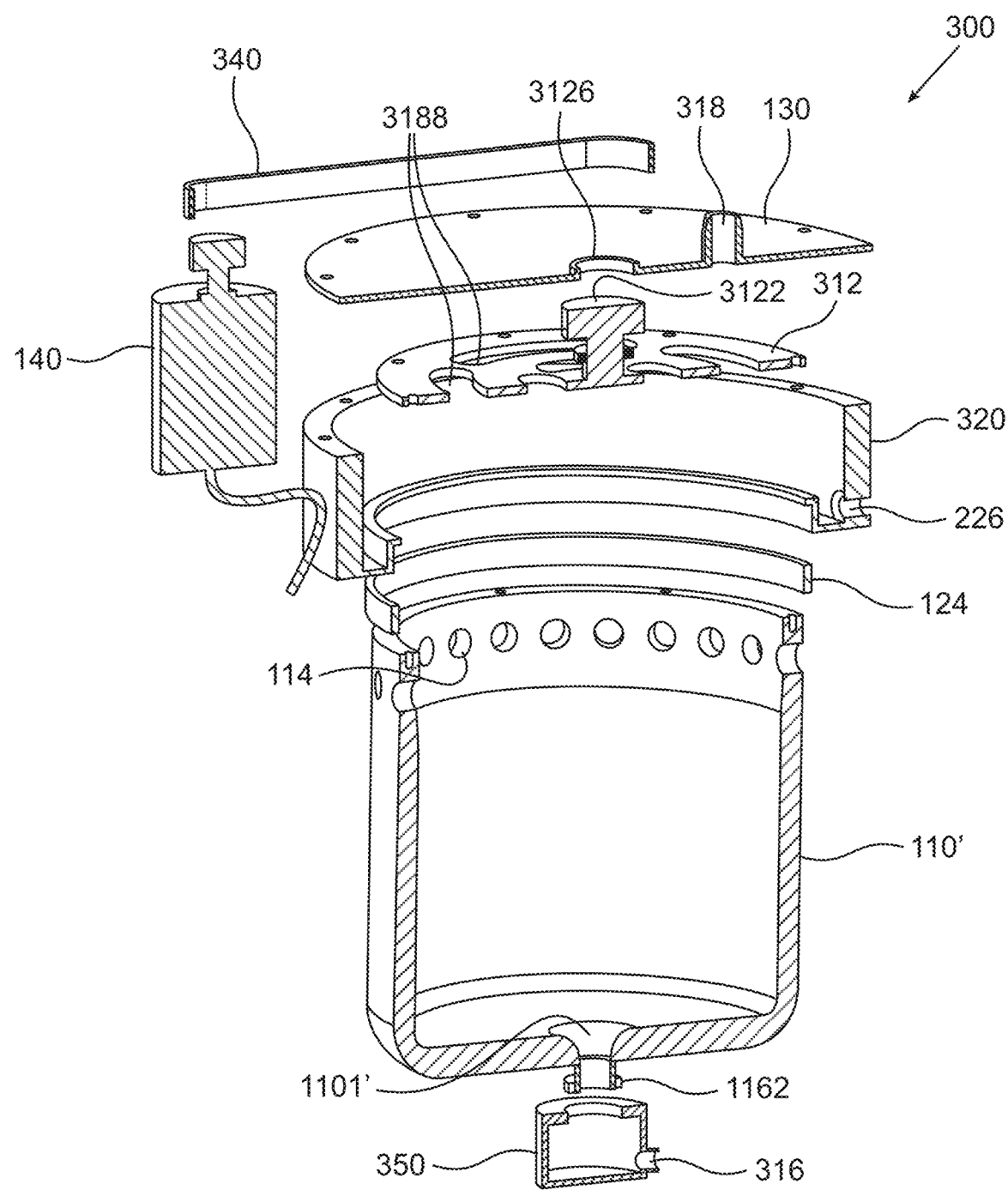

FIGS. 4A-4C are schematic illustrations of one another optional embodiment of a oxygenator 300 in accordance with the present invention having an upper motor 140 connected to the rotating tank by belt 340, wherein FIG. 4A is an isometric view illustration, FIG. 4B is a cross section view illustration, and FIG. 4C is an isometric cross section exploding view illustration.

In the non-limiting example illustrated in these drawings, oxygenator 300 comprises cylindrical rotating tank 110' that is connected at the bottom to a blood inlet chamber 350 that comprises a blood inlet opening 316 through which, blood from the patient is circulated into oxygenator 300 for gas exchange. Blood inlet chamber 350 is separated from rotating tank 110' by blood inlet bearing 1162 that ensures that the blood inlet chamber 350 will remain stationary although its content flows into a rotating chamber. The inserted blood flows upward thanks to the rotation movement of tank 110' and along this flow the gas exchange occurs in a manner that the blood that reaches blood drainage openings 114 the blood is oxygenated and ready to be circulated back into the patient. The oxygenated blood is collected by blood collecting tank 320 that encompasses the upper portion of rotating tank 110' and remains stationary thanks to collecting tank bearing 124. The collected blood exit through blood exit opening 226 and circulated back to the patient. Additionally, the collecting tank 320 comprises a gas release opening 18 that allows release of the circulated gas out from the oxygenator to the surroundings.

In the specific example illustrated herein, oxygenator 300 does not contain blood inlet tube that enters the inner cavity of rotating tank 110' as illustrated in previous embodiments and the blood inlet chamber 350 replaces it as the blood collected within it is being drawn upward through the bottom section 1101' into rotating tank 110'. The blood may be drawn upward thanks to the circulation movement of tank 110' and/or by a dedicated pump that pushes it upward.

Furthermore, oxygenator 300 does not contain gas tubes as illustrated with reference to previous examples. In this optional embodiment the gas flows into oxygenator 300 through a dedicated inlet 318 comprised in top cover 130 that allows connection of a gas source to oxygenator 300 and flows into the rotating chamber to allow gas exchange with the blood through dedicated openings 3188 on rotating middle plate 312 as will be described in detail hereinbelow.

Top cover 130 serves as the ceiling of blood collecting tank 320, and in addition to the gas inlet it comprises a hole to allow passage of rotating middle plate handle 3122 that is functionally connected to motor 140 via belt 340 and allows the rotation of rotating tank 110'.

Rotating middle plate 312 in this specific embodiment is perforated and comprises at least one opening 3188 that allows gas flow directly from gas inlet 318 of blood collecting tank 320 into rotating tank 110'. The gas flow pathway according to this embodiment is demonstrated by arrow 20 (FIG. 4B) and the blood flow pathway according to this embodiment is demonstrated by doted arrow 30 (FIG. 4B). Rotating middle plate 312 further comprises a protruding handle that exits through opening 3126 of top cover 130. Protruding handle 3122 allows to connect rotating tank 110' to motor 140 and serves as a belt pulley to motor belt 340. It should be clear that the number and position of gas openings 3188 may vary according to desired designs. Similarly, the upper motor 140 may be connected to the rotating tank by other technical solutions other than a motor belt and even with a motor belt it may be connected to more than one belt pulley or any other suitable holding point.

Figure 4D:
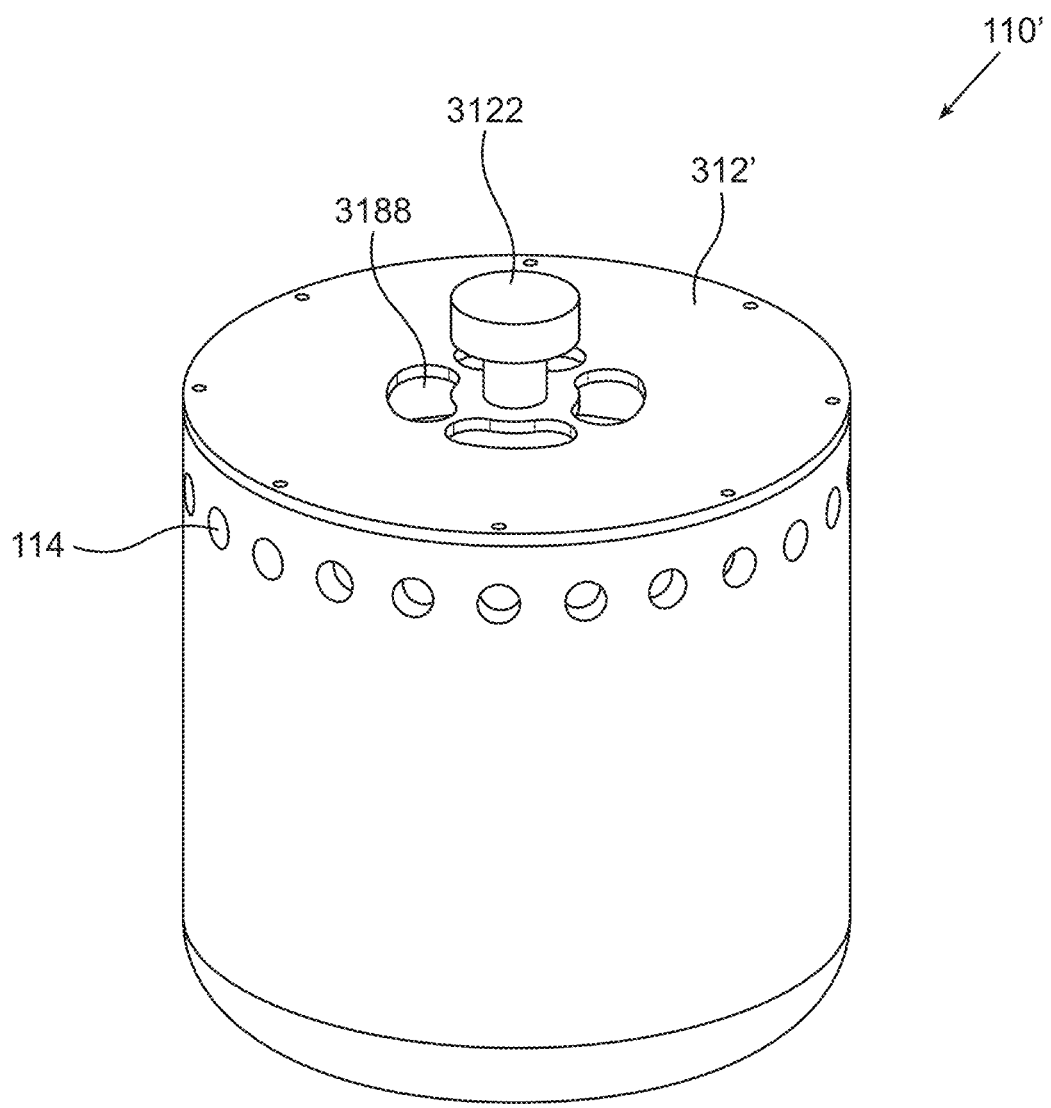
FIG. 4D is an isometric view of the rotating tank of the oxygenator of FIG. 4A having a different gas insertion mechanism in accordance with optional embodiments of the invention.

FIG. 4D is an isometric view of the rotating tank 110' of oxygenator 300 of FIG. 4A having a different shape and distribution of gas openings 3188 of rotating middle plate 312' in accordance with optional non-limiting embodiments of the invention. In this specific design the gas openings are centered around belt pulleys 3122 such that the gas flows mainly at the center of rotating tank 110' at the entrance area to direct the flow of the entered gas toward the circulating blood on the rotating tank wall and to distance the gas from the blood drainage openings 114.

Figure 5A:
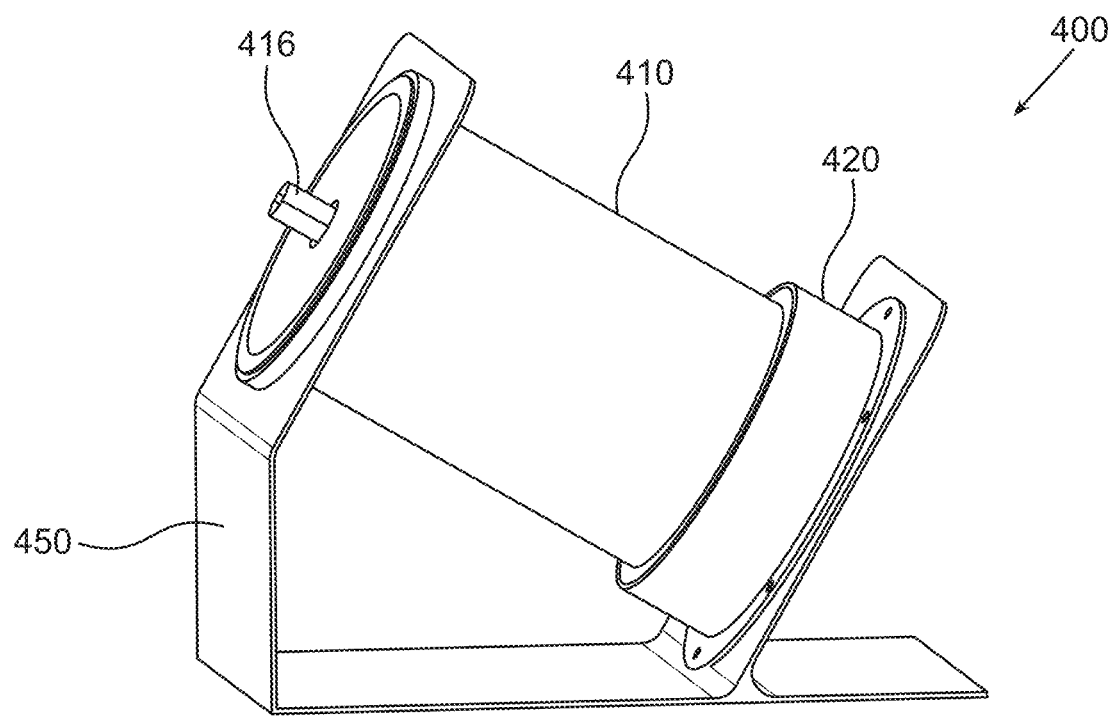
Figure 5B:
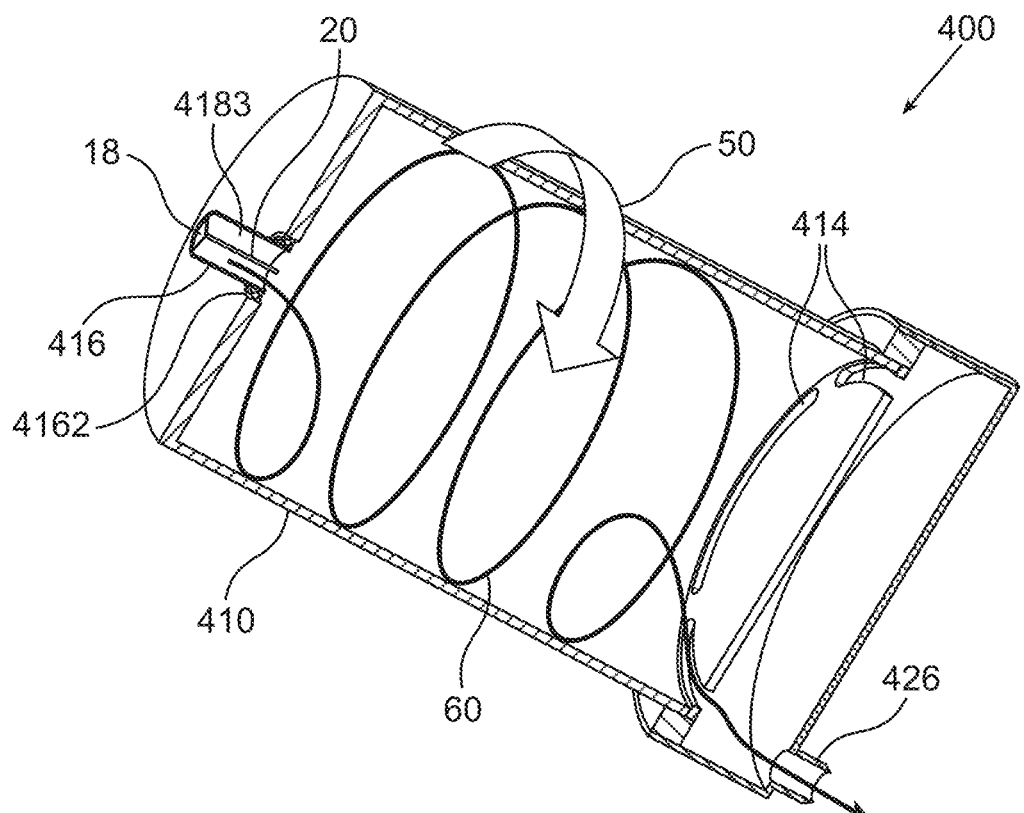

FIGS. 5A-5B are schematic illustrations showing the oxygenator assembly 400 of the invention according to any embodiment illustrated above positioned leaning on a stand 450 in a manner that creates an angle between the blood entered the rotating tank through blood inlet 416 and the tank wall 410.

FIG. 5A is an isometric side view illustration of oxygenator 400 assembly tilted on stand 450. In the specific configuration described herein the blood enters into rotating chamber 410 from top. The entry of blood and gas into oxygenator 400 is made in the non-limiting example illustrated herein through a split tube 20 divided into 3 sub-tubes: gas entry tube 4183, blood entry tube 416, and gas release tube 18. Split tube 20 is functionally connected to rotating tank 410 by bearing 4162 that keeps the tube stationary, despite the rotation movement of tank 410. The entered blood flows downward until it reaches slots 414 and spills into blood collecting chamber 420 and exit from oxygenator 400 through blood exit 426 that is connected to a tube (not shown).

FIG. 5B is a schematic cross section view illustration of the assembly of FIG. 5A showing the tank rotation direction by arrow 50 and the blood flow direction from entrance to exit by arrow 60. The slope between the oxygenator and the surface causes the inserted blood to hit the wall of the rotating tank upon entrance, and not to hit the bottom of the tank as described with reference to previous embodiments above. Thus, the inserted blood flows along the tank wall from the point that it hits the wall downward while gas exchange occurs during this flow, until it reaches the blood exit slots 414 of rotating tank 410, where the oxygenated blood is spilled into the blood collecting tank and exits oxygenator 400 via a tube connected to blood outlet 426. The rotational motion of the container produces a situation in which blood is smeared on the rotating tank wall in a thin layer and flows downward slower as the rotation movement applies physical force against the gravity force.

It should be clear that the description of the embodiments and attached Figures set forth in this specification serves only for a better understanding of the invention, without limiting its scope. It should also be clear that a person skilled in the art, after reading the present specification could make adjustments or amendments to the attached Figures and above-described embodiments that would still be covered by the present invention.

The invention claimed is:

1. A blood-gas exchange device comprising:
   a. a stationary blood collecting tank, said stationary blood collecting tank surrounds at least part of a rotating tank, and comprises at least a gas inlet configured to allow flow of gas into the blood-gas exchange device, a gas exit configured to allow exit of gas out from the blood-gas exchange device; and a blood exit configured to allow flow of oxygenated and/or decarbonated blood out from the blood-gas exchange device into a tube;
   b. a rotating tank, said rotating tank comprises at least: a gas inlet and a blood inlet for insertion of blood and gas flow into the blood-gas exchange device for oxygenating the inserted blood and/or for removing carbon dioxide from the inserted blood; and at least one blood exit opening for removing the oxygenated and/or decarbonated blood out from the rotating tank into the stationary collecting tank; and
   c. a motor configured to spin said rotating tank;

wherein, the circular movement of the rotating tank channels the inserted blood to flow along the rotatable tank wall from bottom to top, forming a blood layer on the wall that directly contacts with the gas and allows gas exchange; and wherein the stationary blood collecting tank is assembled with the rotating tank in a manner that the oxygenated and/or decarbonated blood that exit from the rotating tank through said at least one exit opening is being spilled into the stationary collecting tank and gathered to flow into a tube.

2. The blood-gas exchange device according to claim 1, wherein the stationary blood collecting tank and the rotating tank are separated by at least one bearing that allows the stationary blood collecting tank to remain static.

3. The blood-gas exchange device according to claim 2, wherein said bearing allows transfer of gas from the rotating tank into the stationary blood collecting tank so as to allow release of the gas to the surroundings.

4. The blood-gas exchange device according to claim 1, further comprising a blood inlet chamber that is functionally connected to said rotating chamber and configured to allow insertion of blood into said rotating tank from the bottom.

5. The blood-gas exchange device according to claim 1, wherein said rotating tank topping comprises at least one gas opening configured to allow the gas inserted through the blood collecting tank to flow into the rotating tank so as to allow gas exchange with the flowing blood, and further to allow exit of gas following the gas exchange with the blood back into said blood collecting tank for release of the gas to the surroundings.

6. The blood-gas exchange device according to claim 1, wherein said stationary collecting tank is fully surrounding said rotating tank, and further comprising a blood inlet for insertion of blood into the rotating tank for oxygenating the blood and/or for removing carbon dioxide from the blood.

7. The blood-gas exchange device according to claim 6, wherein the blood is inserted into the blood-gas exchange device from said blood inlet of said stationary blood collecting tank, flowed into the rotating tank for gas exchange, and returns to the blood collecting tank upon oxygenation and/or removal of carbon dioxide and gathered to flow into a tube.

8. The blood-gas exchange device according to claim 1, wherein said blood layer is either one of a blood channel or a blood film formed by the circular movement of the rotatable tank.

9. The blood-gas exchange device according to claim 1, wherein said blood layer flows upward against gravity force by the circular movement of the rotatable tank.

10. The blood-gas exchange device according to claim 1, wherein said gas inlet is configured to insert into the blood-gas exchange device either one of the following gases: pure oxygen, air, enriched air with oxygen at various ratios, nitrogen, carbon dioxide and mixture thereof.

11. The blood-gas exchange device according to claim 1, further comprising at least one perforated gas column configured to inflow the gas inserted through the gas inlet of the stationary blood collecting tank into the rotating tank, said at least one perforated gas column is positioned within the rotating tank cavity and allows flow of gas from the column toward the flowing blood.

12. The blood-gas exchange device according to claim 1, wherein said gas exchange is either oxygenation of the blood or decarbonation of the blood or a combination thereof.

13. The blood-gas exchange device according to claim 1, wherein said blood inlet and blood exit, each is connected to a tube that delivers blood from a blood source and/or from a storage container into the blood-gas exchange device and return the blood to the blood source and/or to a storage container following the gas exchange via the blood exit.

14. The blood-gas exchange device according to claim 13, further comprising at least one pump configured to withdraw blood from said blood source or from the storage container into the blood-gas exchange device and to transfer the oxygenated/decarbonated blood back to the blood exit.

15. The blood-gas exchange device according to claim 1, wherein said flow of gas through the gas inlet and exit of gas through the gas exit is continuous and allows a gradient flow of gases within the blood-gas exchange device that enables gases from the blood to diffuse into the rotatable tank and gases from the rotatable tank to diffuse into the flowing blood.

16. A blood-gas exchange device according to claim 1, wherein instead of blood another body fluid is inserted for gas exchange procedure.

* * * * *